US010266510B2

(12) United States Patent
Al-Zaydi et al.

(10) Patent No.: US 10,266,510 B2
(45) Date of Patent: Apr. 23, 2019

(54) ANTIMICROBIAL AND CYTOTOXIC COMPOUNDS AND METHODS FOR TREATING CANCER, A BACTERIAL INFECTION, AND/OR A FUNGAL INFECTION

(71) Applicant: King Abdulaziz University, Jeddah (SA)

(72) Inventors: Khadijah M. Al-Zaydi, Jeddah (SA); Tamer S. Saleh, Jeddah (SA); Enas Nabil Danial Mahdy, Jeddah (SA); Mohamed H. Elnagdi, Jeddah (SA)

(73) Assignee: King Abdulaziz University, Jeddah (SA)

( * ) Notice: Subject to any disclaimer, the term of this patent is extended or adjusted under 35 U.S.C. 154(b) by 73 days.

(21) Appl. No.: 15/409,175

(22) Filed: Jan. 18, 2017

(65) Prior Publication Data

US 2018/0201598 A1 Jul. 19, 2018

(51) Int. Cl.
*C07D 311/56* (2006.01)

(52) U.S. Cl.
CPC ................... *C07D 311/56* (2013.01)

(58) Field of Classification Search
CPC .................................................. C07D 311/56
See application file for complete search history.

(56) References Cited

U.S. PATENT DOCUMENTS

| 7,968,586 B2 | 6/2011 | Gangwar |
| 2015/0011618 A1 | 1/2015 | Ding et al. |

FOREIGN PATENT DOCUMENTS

| CN | 103896902 A | 7/2014 |
| CN | 103980287 A | 8/2014 |
| GB | 1357633 A | 3/1971 |
| SK | 116092 A3 | 4/1992 |

OTHER PUBLICATIONS

Hadda, T.B., et al. "Structure and POM analyses of 2-{(2Z)-2-[(2R)-2-ethoxy-4-oxo-2H-chromen-3(4H)-ylidene]hydrazinyl}benzonitrile with promising parasitological activity." Res Chem Intermed. (2016), vol. 42, pp. 2201-2210.*
Brooks, James D. "Translational genomics: The challenge of developing cancer biomarkers." Genome Research. © 2012. vol. 22, pp. 183-187.*
Henry, N. Lynn, et al. "Cancer biomarkers." Molecular Oncology. (2012), vol. 6, pp. 140-146.*

American Cancer Society. "Six Ways to Lower Your Risk for Colorectal Cancer." © 2018. Available from: < https://www.cancer.org/latest-news/six-ways-to-lower-your-risk-for-colon-cancer.html >.*
Mayo Clinic. "Breast cancer prevention: How to reduce your risk." © 2018. Available from: < https://www.mayoclinic.org/healthy-lifestyle/womens-health/in-depth/breast-cancer-prevention/art-20044676 >.*
American Cancer Society. "Can Liver Cancer Be Prevented?" © 2018. Available from: < https://www.cancer.org/cancer/liver-cancer/causes-risks-prevention/prevention.html >.*
Al-Zaydi, K., et al. "Structure and POM analyses of 2-{(2Z)-2-[(2R)-2-ethoxy-4-oxo-2H-chromen-3(4H)-ylidene]hydrazinyl}benzonitrile with promising parasitological activity." Res Chem Intermed. (2016), vol. 42, pp. 2201-2210. (Year: 2016).*
K. Al-Zaydi, et al., "Studies With Enaminones: Formation of a N,O-Cyclicacetal on Coupling of 3-Dimethylamino-1-hydroxyphenyl-2-propenone with Arenediazonium Salts" J. Heterocyclic Chem., vol. 44, 2007, pp. 1187-1189.
K. Hayashi, et al., "Antiviral Targets of a Chromene Derivative from Sargassum Micracanthum in the Replication of Human Cytomegalovirus" Biol. Pharm. Bull., vol. 29, Issue. 9, 2006 pp. 1843-1847.
Y. Shishido, et al., "Discovery and stereoselective synthesis of the novel isochroman neurokinin-1 receptor antagonist 'CJ-17,493'" Bioorganic & Medicinal Chemistry, vol. 16, 2008, pp. 7193-7205.
W. Wang, et al., "Novel 1, 3-Disubstituted-5, 10-Dihydro-5, 10-Dioxo-1H-Benzo[G] Isochromene-3 Carboxamides as Potent Antitumor Agents" Bioorganic & Medicinal Chemistry Letters, vol. 8, 1998, pp. 1579-1584.
B. China Raju, et al., "Synthesis, structure-activity relationship of novel substituted 4H-chromen-1,2,3,4-tetrahydropyrimidine-5-carboxylates as potential anti-mycobacterial and anticancer agents" Bioorganic & Medicinal Chemistry Letters, vol. 21, 2011, pp. 2855-2859.
E. Venkateswararao, et al., "Synthesis and SAR Studies of Bis-Chromenone Derivatives for Anti-prolifera-tive Activity against Human Cancer Cells" Bioorganic & Medicinal Chemistry Letters, 2014, pp. 1-16.
S. Moorkoth, "Synthesis and Anti-cancer Activity of Novel Thiazolidinone Analogs of 6-Aminoflavone" Chem. Pharm. Bull., vol. 63, Issue. 12 2015, pp. 974-985.
S. Alam, "Synthesis, antibacterial and antifungal activity of some derivatives of 2-phenyl-chromen-4-one" J. Chem. Sci., vol. 116, Issue. 6, Nov. 2004, pp. 325-331.
V. Barve, et al., "Synthesis, Molecular Characterization, and Biological Activity of Novel Synthetic Derivatives of Chromen-4-one in Human Cancer Cells" J. Med. Chem., 2006, vol. 49, pp. 3800-3808.

(Continued)

*Primary Examiner* — Andrew D Kosar
*Assistant Examiner* — John S Kenyon
(74) *Attorney, Agent, or Firm* — Oblon, McClelland, Maier & Neustadt, L.L.P.

(57) ABSTRACT

Small molecules and methods of treating cancer, a bacterial infection, and/or a fungal infection. The small molecules are chromenone derivatives. They have antimicrobial properties and are cytotoxic towards colon, liver, and breast cancer cell lines.

10 Claims, 1 Drawing Sheet

(56) References Cited

OTHER PUBLICATIONS

S. Aiello, et al., "Synthesis and Biological Properties of Benzothiazole, Benzoxazole, and Chromen-4-one Analogues of the Potent Antitumor Agent 2-(3,4-Dimethoxyphenyl)-5-fluorobenzothiaole (PMX 610, NSC 721648)1" J. Med. Chem. 2008, vol. 51, pp. 5135-5139.
C. Cano, et al., "DNA-Dependent Protein Kinase (DNA-PK) Inhibitors. Synthesis and Biological Activity of Quinolin-4-one and Pyridopyrimidin-4-one Surrogates for the Chromen-4-one Chemotype" J. Med. Chem., 2010, vol. 53, pp. 8498-8507.
R. Mancuso, et al., "A Simple and Mild Synthesis of 1H-Isochromenes and (Z)-1-Alkylidene-1,3-dihydroisobenzofurans by the Iodocyclization of 2-(1-Alkynyl)benzylic Alcohols" J. Org. Chem. 2010, vol. 75, 897-901.
K. Moritmoto, et al., "Synthesis of Isochromene and Related Derivatives by Rhodium-Catalyzed Oxidative Coupling of Benzyl and Allyl Alcohols with Alkynes" The Journal of Organic Chemistry, 2011, vol. 76, pp. 9548-9551.
M. Liu, et al., "A Novel Lignanoid and Norbisabolane Sesquiterpenoids from Glochidion puberum" Chemistry of Natural Compounds, vol. 44, No. 5, 2008, pp. 588-590.
A. Lazarenkow, et al., "The influence of chromone base hydrozones on lipid peroxidation and bFGF concentration in the HL-60 cell line." Acta Biochim Pol. vol. 60, Issue. 2, 2013, pp. 1.
Z. Dongnuan, et al., "Microwave-Assisted Ionic Liquid Catalyzed One-Pot Three-Component Synthesis of 3-(1-[2-(4-Arylthiazol-2-yl)-hydrazono]ethyl)-2H-chromen-2-one" Chin. J.Org. Chem. , vol. 32, Issue. 9, 2012, pp. 1732-1735.

* cited by examiner

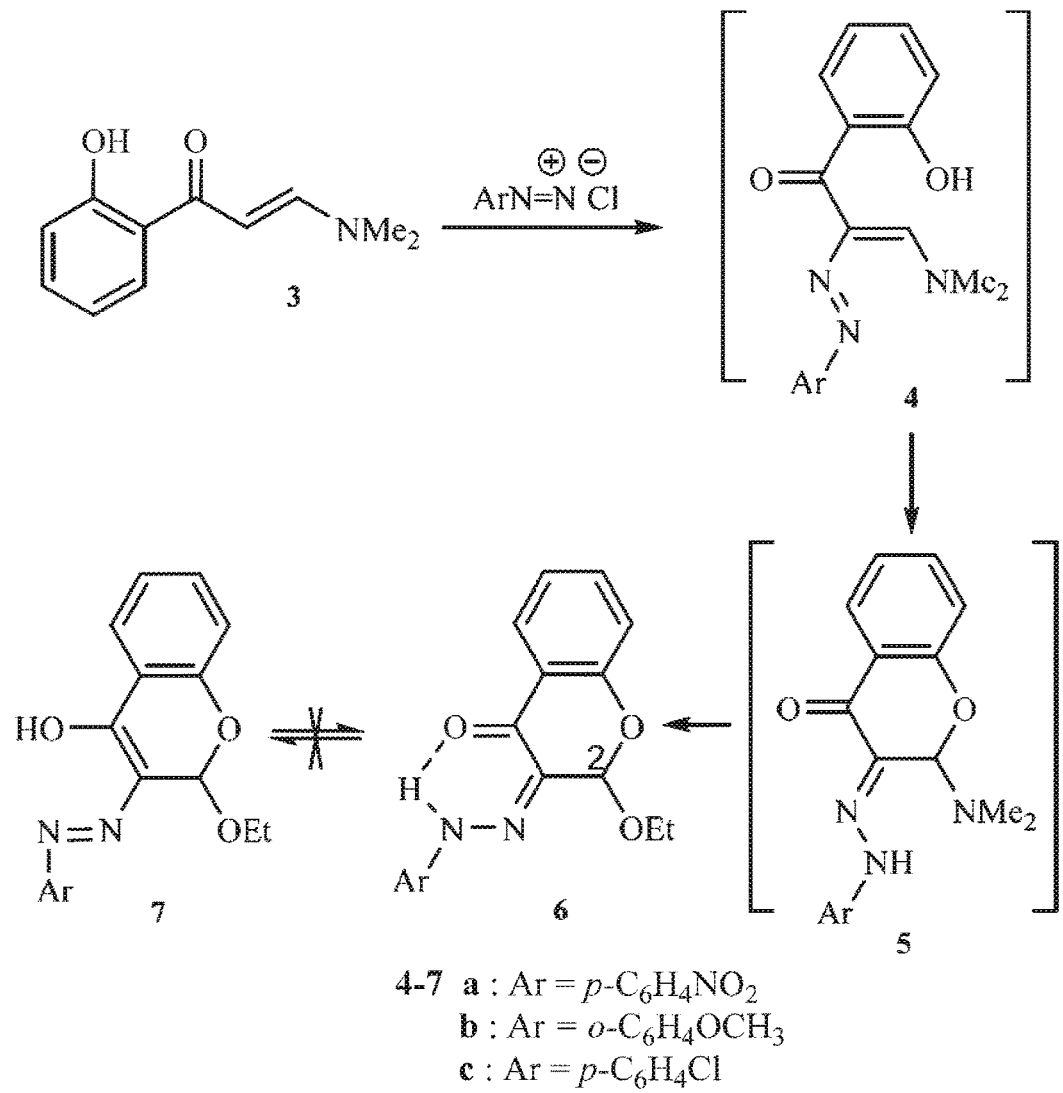

ANTIMICROBIAL AND CYTOTOXIC COMPOUNDS AND METHODS FOR TREATING CANCER, A BACTERIAL INFECTION, AND/OR A FUNGAL INFECTION

BACKGROUND OF THE DISCLOSURE

Technical Field

The present disclosure relates to antimicrobial and cytotoxic small molecules and methods for treating some types of cancer, a bacterial infection, and/or a fungal infection.

DESCRIPTION OF THE RELATED ART

Compounds based on the chromenone framework are found in a variety of natural products, bioactive molecules, and pharmaceuticals (S. Alam, J. Chem. Sci. 116, 325 (2004); S. Aiello, G. Wells, E. L. Stone, H. Kadri, R. Bazzi, D. R. Bell, M. F. G. Stevens, C. S. Matthews, T. D. Bradshaw, A. D. Westwell, J. Med. Chem. 51, 5135 (2008); V. Barve, F. Ahmed, S. Adsule, S. Banerjee, S. Kulkarni, P. Katiyar, C. E. Anson, A. K. Powell, S. Padhye, F. H. Sarkar, J. Med. Chem. 49, 3800 (2006); C. Cano, O. R. Barbeau, C. Bailey, X. L. Cockcroft, N.J. Curtin, H. Duggan, M. Frigerio, B. T. Golding, I. R. Hardcastle, M. G. Hummersone, C. Knights, K. A. Menear, D. R. Newell, C. J. Richardson, G. C. M. Smith, B. Spittle, R. J. Griffin, J. Med. Chem. 53, 8498 (2010); and K. Hayashi, K. Mori, H. Saito, T. Hayashi, Biol. Pharm. Bull. 29, 1843 (2006), each incorporated herein by reference in their entirety). They have important biological effects including antitumor properties (W. Wang, T. Li, R. Milburn, J. Yates, E. Hinnant, M. J. Luzzio, S. A. Noble, G. Attardo, Bioorg. Med. Chem. Lett, 8, 1579 (1998); Y. Shishido, H. Wakabayashi, H. Koike, N. Ueno, S. Nukui, T. Yamagishi, Y. Murata, F. Naganeo, M. Mizutani, K. Shimada, Y. Fujiwara, A. Sakakibara, O. Suga, R. Kusano, S. Ueda, Y. Kanai, M. Tsuchiya, M. Satake, Bioorg. Med. Chem. 16, 7193 (2008); and M. Liu, H.-T. Xiao, H.-P. He, X.-Y. Hao, Chem. Nat. Compd. 44, 588 (2008), each incorporated herein by reference in their entirety). The quantitative relationship between its chemical structure and biological activity has received considerable attention in recent years. The important biological effects of chromenone derivatives encourage the synthetic organic chemists to discover an efficient and versatile synthesis for chromenone derivatives (K. Morimoto, K. Hirano, T. Satoh, M. Miura, J. Org. Chem. 76, 9548 (2011); and R. Mancuso, S. Mehta, B. Gabriele, G. Salerno, W. S. Jenks, R. C. Larock, J. Org. Chem. 75, 897 (2010), each incorporated herein by reference in their entirety).

A series of 4H-chromen-1,2,3,4-tetrahydropyrimidine-5-carboxylate derivatives were synthesized, screened for their anti-mycobacterial and anti-cancer activities. Compound 1 was found to be an anti-mycobacterial compound, and compound 2 was found to be a potent anti-cancer agent. These compounds were model compounds for the design and development of therapeutics with anti-mycobacterial and anti-cancer activity (FIG. 1) (B. C. Raju, R. N. Rao, P. Suman, P. Yogeeswari, T. B. Shaik, S. V. Kalivendi, D. Sriram, Bioorganic & Medicinal Chemistry Letters 21, 2855, (2011), incorporated herein by reference in its entirety).

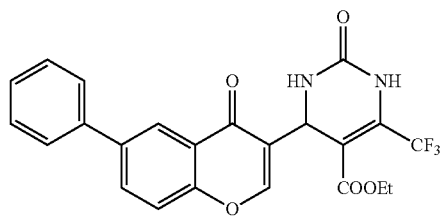

1

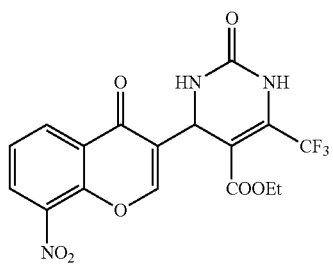

2

A novel family of 3-((4-oxo-4H-chromen-3-yl)methyl)-4H-chromen-4-one (bis-chromone) derivatives were designed, synthesized, and studied for their anti-cancer activity using the XTT assay for the growth inhibition against various human cancer cells. The structure-activity studies indicated bis-chromone can be used as a basic scaffold to design anti-cancer agents represented by formula (A) (E. Venkateswararao, V. K. Sharma, M. Manickam, J. Yun, S. H. Jung, Bioorganic & Medicinal Chemistry Letters, 24, 5256 (2014), incorporated herein by reference in its entirety). A 5-cyclohexylmethoxy group on the first chromenone ring and an electron-donating group, such as $CH_3$, $OCH_3$, or a hydrogen bonding group (OH), on the other chromenone ring of bis-chromone increased the activity. However, saturation of one of the chromenone moiety to chroman-one in bis chromones decreased the activity.

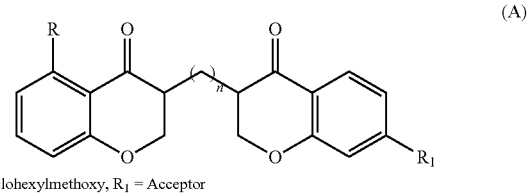

(A)

R = cyclohexylmethoxy, $R_1$ = Acceptor

Chromenone compounds represented by formula (B), a pharmaceutically accepted salt thereof, or a prodrug thereof have been studied by Beijing Shenogen Pharma group as antitumor agents (H. Ding, J. Li, K. Meng, US Patent, 2015/0011618A1 (2015), incorporated herein by reference in its entirety).

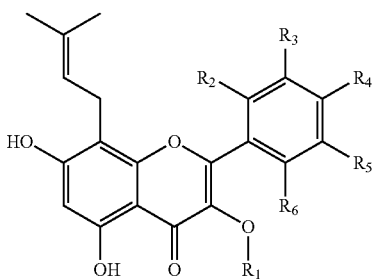

(B)

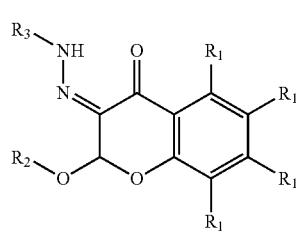

(I)

The anti-cancer activity of trifluoromethylated chromenone (flavonoid) analogues were studied (R. B. Patil, S. D. Sawant, IJAPBC, 1, 72 (2012), incorporated herein by reference in its entirety).

Compounds represented by formula (C) were synthesized by combining a flavone nucleus and a thiazolidinone ring in an effort to potentiate the existing anti-cancer activity of flavone (S. Moorkoth, Chem. Pharm. Bull. 63, 974 (2015), incorporated herein by reference in its entirety).

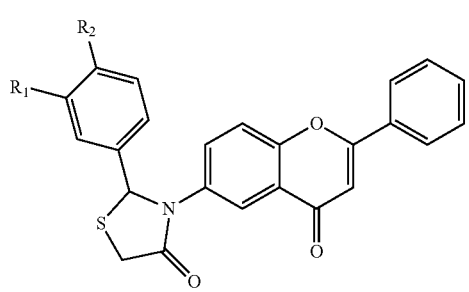

(C)

Many therapeutic agents, especially those agents which are effective in cancer chemotherapy, often exhibit acute in vivo toxicity such as bone marrow toxicity, mucosal toxicity, chronic cardiac toxicity, and neurological toxicity. Such high toxicity can limit their applications. In addition, such agents have limited stability in plasma.

Therefore, an objective of this disclosure is to provide a stable small molecule with antimicrobial and cytotoxic properties and a method for treating cancer, bacterial infection, and/or fungal infection.

BRIEF SUMMARY

The foregoing paragraphs have been provided by way of general introduction, and are not intended to limit the scope of the following claims. The described embodiments, together with further advantages, will be best understood by reference to the following detailed description taken in conjunction with the accompanying drawings.

A first aspect of the disclosure relates to a method for treating at least one of a cancer, a bacterial infection, and a fungal infection in a subject in need thereof, the method comprising administering an effective amount of a compound of formula (I), which has antimicrobial and cytotoxic properties:

a salt thereof, a solvate thereof, or a combination thereof, to the subject in need thereof, where each of $R_1$ is independently selected from the group consisting of H, hydroxy, amino, thiol, fluoro, chloro, bromo, iodo, cyano, carboxy, an optionally substituted carbamyl, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted hydrocarbyl, an optionally substituted heteroarylcarbonyl, an optionally substituted arylolefin, an optionally substituted arylalkylcarboxylic acid, and an optionally substituted vinyl, $R_2$ selected from the group consisting of an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted heteroarylcarbonyl, an optionally substituted arylolefin, or an optionally substituted vinyl, and $R_3$ is an optionally substituted aryl.

In one embodiment, $R_2$ is an optionally substituted alkyl.

In one embodiment, $R_3$ is a substituted phenyl comprising an electron withdrawing functional group.

In one embodiment, the electron withdrawing functional group is at least one selected from the group consisting of fluoro, chloro, bromo, iodo, nitro, cyano, ammonium, an optionally substituted alkylammonium, an optionally substituted arylammonium, an optionally substituted alkylarylammonium, trihalomethyl, formyl, an optionally substituted alkanoyl, an optionally substituted aroyl, and sulfonate.

In one embodiment, $R_1$ is H, $R_2$ is ethyl, and $R_3$ is selected from the group consisting of p-$C_6H_4NO_2$, o-$C_6H_4OCH_3$, and p-$C_6H_4Cl$.

In one embodiment, the method further comprises measuring a concentration of a biomarker before and/or after the compound of formula (I), the salt thereof, the solvate thereof, or the combination thereof is administered.

In one embodiment, the biomarker is at least one selected from the group consisting of AFP, BCR-ABL, BRCA1, BRCA2, BRAF, CA-125, CA19.9, CEA, EGFR, HER-2, KIT, PSA, S100, KRAS, p53, p16, CDKN2B, p14ARF, MYOD1, CDH1, CDH13, RB1, metallopeptidase inhibitor 1, microRNA, estrogen receptor, progesterone receptor, UGT1A1, CD20 antigen, CD30, PDGFR, leucine, isoleucine, valine, ALK, galactomannan, 1,3-β-D-glucan, C-reactive protein, soluble triggering receptor expressed on myeloid cells 1, pro-adrenomedullin, serum procalcitonin, mid-regional pro-atrial natriuretic peptide, pancreatic stone protein, regenerating protein, interleukin-6, IL-8, IL-27, soluble urokinase-type plasminogen activator receptor.

In one embodiment, the concentration of the biomarker is measured with an ELISA assay.

In one embodiment, a source of the bacterial infection is at least one gram-positive bacteria selected from the group consisting of *Bacillus subtilits, Staphylococcus aureus*, and *Enterococcus faecalis*, and/or at least one gram-negative bacteria selected from the group consisting of *Escherichia coli, Pseudomonas aeruginosa*, and *Proteus* species.

In one embodiment, a source of the fungal infection is yeast and/or at least one filamentous fungus selected from the group consisting of *Aspergillus niger* and *Aspergillus flavus*.

In one embodiment, the cancer is at least one selected from the group consisting of colon cancer, breast cancer, and liver cancer.

In one embodiment, the subject is a mammal.

In one embodiment, the effective amount of the compound of formula (I), the salt thereof, the solvate thereof, or the combination thereof is in a range of 1-100 mg/kg.

A second aspect of the disclosure relates to a compound of formula (I):

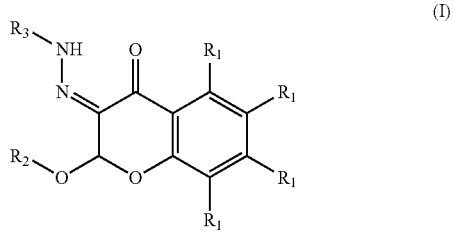

where each of $R_1$ is independently selected from the group consisting of H, hydroxy, amino, thiol, fluoro, chloro, bromo, iodo, cyano, carboxy, an optionally substituted carbamyl, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted hydrocarbyl, an optionally substituted heteroarylcarbonyl, an optionally substituted arylolefin, an optionally substituted arylalkylcarboxylic acid, and an optionally substituted vinyl, $R_2$ selected from the group consisting of an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted heteroarylcabonyl, an optionally substituted arylolefin, or an optionally substituted vinyl, and $R_3$ is an optionally substituted aryl group which excludes p-$C_6H_4NO_2$, o-$C_6H_4OCH_3$, and p-$C_6H_4Cl$.

In one embodiment, $R_2$ is an optionally substituted alkyl group.

In one embodiment, $R_1$ is H, $R_2$ is ethyl, and $R_3$ is a substituted phenyl comprising an electron withdrawing functional group.

In one embodiment, the electron withdrawing functional group is at least one selected from the group consisting of fluoro, bromo, iodo, cyano, ammonium, an optionally substituted alkylammonium, an optionally substituted arylammonium, an optionally substituted alkylarylammonium, trihalomethyl, formyl, an optionally substituted alkanoyl, an optionally substituted aroyl, and sulfonate.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1 is a reaction scheme for multiple embodiments of the compound of formula (I).

DETAILED DESCRIPTION OF THE EMBODIMENTS

Embodiments of the present disclosure will now be described more fully hereinafter with reference to the accompanying drawings, in which some, but not all of the embodiments of the disclosure are shown.

The present disclosure will be better understood with reference to the following definitions.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the terms "treat", "treatment", and "treating" in the context of the administration of a therapy to a subject in need thereof refer to the reduction or inhibition of the progression and/or duration of a disease, the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells/bacteria/fungus and/or tumor size before administration), or elimination of the cancer cells/bacteria/fungus, (2) inhibiting cancerous cell division, cancerous cell proliferation and/or bacteria/fungus growth, (3) relieving to some extent (or, preferably, eliminating) one or more symptoms associated with a pathology related to or caused in part by unregulated or aberrant cellular division and/or bacterial/fungal infection, (4) an increase in disease-free, relapse-free, progression-free, and/or overall survival, duration, or rate, (5) a decrease in hospitalization rate, (6) a decrease in hospitalization length, (7) eradication, removal, or control of bacterial/fungal infection, and/or primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, or bacterial/fungal populations (9) an impairment in the formation of a tumor, bacterial infection, or fungal infection (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The terms "patient", "subject", and "individual" are used interchangeably. As used herein, they refer to individuals suffering from a disease, and encompass mammals and non-mammals. None of the terms require that the individual be under the care and/or supervision of a medical professional. Mammals are any member of the mammalian class, including but are not limited to humans, non-human primates, such as chimpanzees, and other apes and monkey species, farm animals, such as cattle, horses, sheep, goats, swine, domestic animals, such as rabbits, dogs, and cats, laboratory animals including rodents, such as rats, mice and guinea pigs, and the like. Examples of non-mammals include, but are not limited to, birds, fishes, and the like. In some embodiments of the methods and compositions provided herein, the subject is a mammal. In preferred embodiments, the subject is a human.

A subject in need of treatment includes a subject already with the disease, a subject which does not yet experience or exhibit symptoms of the disease, and a subject predisposed to the disease. In preferred embodiments, the subject is a person who is predisposed to cancer, e.g. a person with a family history of cancer. African Americans, Jews of Eastern European descent, or a person with: (i) a personal history of colorectal polyps and/or inflammatory bowel disease, (ii) a family history of adenomatous polyps, (iii) an inherited syndrome (Lynch syndrome, Turcot syndrome, Peutz-Jeghers syndrome, MUTYH-associated polyposis), and/or (iv) type 2 diabetes, are at a higher risk of contracting colon cancer. White women or a person with (i) certain inherited genes (e.g. mutated BRCA1, BRCA2, ATM, TP53, CHEK2, PTEN, CDH1, STK11, and PALB2), (ii) radiation to one's chest, and/or (iii) exposure to diethylstilbestrol (DES), are at a higher risk of contracting breast cancer. Asian Americans, Pacific Islanders, or a person with (i) chronic viral hepatitis (Hep-B or Hep-C), (ii) cirrhosis, (iii) type 2 diabetes, (iv) diseases such as tyrosinemia, alpha1-antitrypsin deficiency, porphyria cutanea tarda, glycogen storage diseases, wilson disease, and/or (v) chronic exposure to aflatoxins, vinyl chloride, and thorium dioxide (Thorotrast), are at a higher risk of contracting liver cancer.

As used herein, the terms "therapies" and "therapy" can refer to any method, composition, and/or active ingredient that can be used in the treatment and/or management of the disease or one or more symptoms thereof. In some embodiments, the method for treating the disease involves the administration of a unit dosage or a therapeutically effective amount of the active ingredient to a subject in need thereof.

The term "active ingredient", as used herein, refers to an ingredient in the composition that is biologically active, for example, the compound of formula (I), a salt thereof, and a solvate thereof.

The terms "effective amount", "therapeutically effective amount", or "pharmaceutically effective amount" refer to that amount of the active ingredient being administered which will relieve to some extent one or more of the symptoms of the disease being treated. The result can be reduction and/or alleviation of the signs, symptoms, or causes of a disease, or any other desired alteration of a biological system. For example, an "effective amount" for therapeutic uses is the amount of the compound of formula (I), the salt thereof, the solvate thereof, or a combination thereof as disclosed herein required to provide a clinically significant decrease in a disease. An appropriate "effective amount" may differ from one individual to another. An appropriate "effective amount" in any individual case may be determined using techniques, such as a dose escalation study.

The dosage and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. In at least one embodiment, the compound of formula (I), the salt thereof, the solvate thereof, or the combination thereof is administered in an effective amount in a range of 1-100 mg/kg based on the weight of the subject, preferably 10-80 mg/kg, more preferably 20-50 mg/kg. In most embodiments, the compound of formula (I), the salt thereof, the solvate thereof, or the combination thereof is formulated in a composition. As used herein, a "composition" refers to a mixture of the active ingredient with other chemical components, such as physiologically acceptable carriers and excipients. One purpose of a composition is to facilitate administration of the compound of formula (I), the salt thereof, the solvate thereof, and a combination thereof to a subject. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The composition thereof may be administered in a single dose or multiple individual divided doses. In some embodiments, the composition is administered at various dosages (e.g. a first dose with an effective amount of 50 mg/kg and a second dose with an effective amount of 10 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, 5 days, 6 days, or 7 days. In certain embodiments, the composition and one or more additional therapies are administered less than 1 day, 1 week, 2 weeks, 3 weeks, 4 weeks, one month, 2 months, 3 months, 6 months, 1 year, 2 years, or 5 years apart.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the compounds and methods described herein. In preferred embodiments, the active ingredient and/or the composition described herein are administered orally.

In other embodiments, the composition has various release rates (e.g. controlled release or immediate release). Immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to the release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the composition is not a controlled-release composition.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration can also involve the use of transdermal administration such as transdermal patches or iontophoresis devices. Formulation of drugs is discussed in, for example, Hoover, John E., Remington's Pharmaceutical Sciences, Mack Publishing Co., Easton, Pa., 1975. Another example of includes Liberman, H. A. and Lachman, L., Eds., Pharmaceutical Dosage Forms, Marcel Decker, New York, N.Y., 1980, which is incorporated herein by reference in its entirety).

The phrase "pharmaceutically acceptable" as used herein refers to counter-ions, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Therefore, the composition refers to the combination of an active ingredient with a carrier, inert or active, making the composition especially suitable for diagnostic or therapeutic use in vivo or ex vivo.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as TWEEN® (ICI, Inc.; Bridgewater, N.J.), polyethylene glycol (PEG), and PLURONICS' (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, "derivative" refers to a chemically or biologically modified version of a chemical compound that is structurally similar to a parent compound and (actually or theoretically) derivable from that parent compound. A "derivative" differs from an "analog" in that a parent compound may be the starting material to generate a "derivative", whereas the parent compound may not necessarily be used as the starting material to generate an "analog". A derivative may or may not have different chemical or physical properties of the parent compound. For example, the derivative may be more hydrophilic or it may have altered reactivity compared to the parent compound. Derivatization (i.e. modification) may involve substitution of one or more moieties within the molecule (e.g. a change in functional group). The term "derivative" also includes conjugates, and prodrugs of a parent compound (i.e. chemically modified derivatives which can be converted into the original compound under physiological conditions).

As used herein, the term "analog" refers to a chemical compound that is structurally similar to a parent compound, but differs slightly in composition (e.g. at least one atom or functional group is different, added, or removed). The analog may or may not have different chemical or physical properties than the original compound and may or may not have improved biological and/or chemical activity. For example, the analog may be more hydrophilic or it may have altered reactivity compared to the parent compound. The analog may mimic the chemical and/or biological activity of the parent compound (i.e. it may have similar or identical activity), or, in some cases, may have increased or decreased activity. The analog may be a naturally or non-naturally occurring variant of the original compound. Other types of analogs include isomers (enantiomers, diastereomers, and the like) and other types of chiral variants of a compound, as well as structural isomers.

As used herein, a "binder" holds the ingredients in a tablet together. Binders ensure that tablets and granules can be formed with required mechanical strength, and give volume to low active dose tablets. Binders may be: (1) saccharides and their derivatives, such as sucrose, lactose, starches, cellulose or modified cellulose such as microcrystalline cellulose, carboxymethyl cellulose, and cellulose ethers such as hydroxypropyl cellulose (HPC), and sugar alcohols such as xylitol, sorbitol or maltitol, (2) proteins such as gelatin, and (3) synthetic polymers including polyvinylpyrrolidone (PVP), polyethylene glycol (PEG). Binders are classified according to their application. Solution binders are dissolved in a solvent (for example water or alcohol can be used in wet granulation processes). Examples include gelatin, cellulose, cellulose derivatives, polyvinylpyrrolidone, starch, sucrose, and polyethylene glycol. Dry binders are added to the powder blend, either after a wet granulation step, or as part of a direct powder compression (DC) formula. Examples include cellulose, methyl cellulose, polyvinylpyrrolidone and polyethylene glycol.

The term "solvate" means a physical association of the compound of formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution-phase and isolable solvates. Exemplary solvates include, but are not limited to, hydrates, ethanolates, methanolates, and isopropanolates. Methods of solvation are generally known in the art.

The term "pharmaceutically acceptable salt" refers to a protonated form of the compound of formula (I) (e.g. an embodiment of the compound of formula (I) with a basic substituent such as an optionally substituted amino group) with a counter-ion. As used herein, the term "counter-ion" refers to an anion, preferably a pharmaceutically acceptable anion that is associated with the protonated form of the compound of formula (I). Non-limiting examples of pharmaceutically acceptable counter-ions include halides, such as fluoride, chloride, bromide, iodide, nitrate, sulfate, phosphate, amide, methanesulfonate, ethanesulfonate, p-toluenesulfonate, salicylate, malate, maleate, succinate, tartrate, citrate, acetate, perchlorate, trifluoromethanesulfonate (triflate), acetylacetonate, hexafluorophosphate, and hexafluoroacetylacetonate. In some embodiments, the counter-ion is a halide, preferably chloride.

In most embodiments, the composition comprises at least 0.5 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 99 wt %, or 99.9 wt %, of the compound of formula (I). Preferably, the composition may further comprise binders, such as sucrose, lactose, xylitol, and excipients such as calcium carbonate, calcium phosphate, and dimethyl sulfoxide (DMSO). A concentration of the compound of formula (I), the salt thereof, the solvate thereof, or the combination thereof in the composition may be in a range of 0.1-10,000 µg/ml, 1-1,000 µg/ml, or 10-1,000 µg/ml.

The salt thereof and/or the solvate thereof may be administered to the subject in addition to the compound of formula (I), which is not in a salt or solvated form (e.g. the composition may comprise 0.5-100 wt %, 10-70 wt %, 10-30 wt %, 10-20 wt %, or 10-15 wt % of the salt thereof and/or the solvate thereof relative to a total weight of the active ingredient).

The first aspect of the disclosure relates to a method for treating at least one of a cancer, a bacterial infection, and a fungal infection in a subject in need thereof the method comprising administering an effective amount of the compound of formula (I):

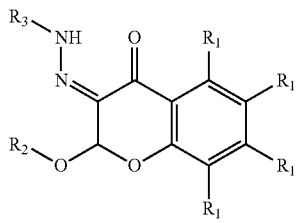

a salt thereof, a solvate thereof, or a combination thereof, to the subject in need thereof, where each of $R_1$ may be H, hydroxy, amino, thiol, fluoro, chloro, bromo, iodo, cyano, carboxy, an optionally substituted carbamyl, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted hydrocarbyl, an optionally substituted heteroarylcarbonyl, an optionally substituted arylolefin, an optionally substituted arylalkylcarboxylic acid, and an optionally substituted vinyl, $R_2$ may be an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted heteroarylcarbonyl, an optionally substituted arylolefin, or an optionally substituted vinyl, and $R_3$ is an optionally substituted aryl.

In one embodiment, $R_2$ is an optionally substituted alkyl. In another embodiment, $R_3$ is a substituted phenyl comprising an electron withdrawing functional group (e.g. fluoro, chloro, bromo, iodo, nitro, cyano, ammonium, an optionally substituted alkylammonium, an optionally substituted arylammonium, an optionally substituted alkylarylammonium, trihalomethyl, formyl, an optionally substituted alkanoyl, an optionally substituted aroyl, and sulfonate). In a preferred embodiment, $R_1$ is H, $R_2$ is ethyl, and $R_3$ is p-$C_6H_4NO_2$, o-$C_6H_4OCH_3$, or p-$C_6H_4Cl$.

The second aspect of the disclosure relates to a compound of formula (I):

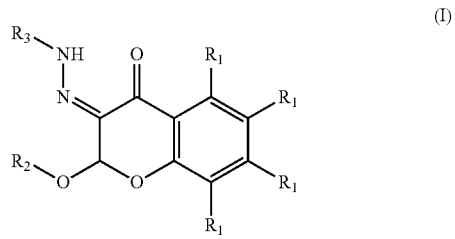

where each of $R_1$ is independently selected from the group consisting of H, hydroxy, amino, thiol, fluoro, chloro, bromo, iodo, cyano, carboxy, an optionally substituted carbamyl, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted heteroarylcarbonyl, an optionally substituted arylolefin, an optionally substituted arylalkylcarboxylic acid, and an optionally substituted vinyl, $R_2$ selected from the group consisting of an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted heteroarylcarbonyl, an optionally substituted arylolefin, or an optionally substituted vinyl, and $R_3$ is an optionally substituted aryl group which excludes p-$C_6H_4NO_2$, o-$C_6H_4OCH_3$, and p-$C_6H_4Cl$.

In one embodiment, $R_1$ is H, $R_2$ is ethyl, and $R_3$ is a substituted phenyl comprising an electron withdrawing functional group. In one embodiment, the electron withdrawing functional group is at least one selected from the group consisting of fluoro, bromo, iodo, ammonium, an optionally substituted alkylammonium, an optionally substituted arylammonium, an optionally substituted alkylarylammonium, trihalomethyl, formyl, an optionally substituted alkanoyl, an optionally substituted aroyl, and sulfonate. In one embodiment, $R_3$ is o-$C_6H_4NO_2$, m-$C_6H_4NO_2$, o-$C_6H_4Cl$, or m-$C_4H_4Cl$.

The term "alkyl", as used herein, unless otherwise specified, refers to a straight, branched, or cyclic hydrocarbon fragment. Non-limiting examples of such hydrocarbon fragments include methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. As used herein, the term "cyclic hydrocarbon" refers to a cyclized alkyl group. Exemplary cyclic hydrocarbon (i.e. cycloalkyl) groups include, but are not limited to, cyclopropyl, cyclobutyl, cyclopentyl, cyclohexyl, norbornyl, and adamantyl. Branched cycloalkyl groups, such as exemplary 1-methylcyclopropyl and 2-methylcyclopropyl groups, are included in the definition of cycloalkyl as used in the present disclosure.

The term "aryl", as used herein, and unless otherwise specified, refers to phenyl, biphenyl, naphthyl, anthracenyl, and the like. The term "heteroaryl" refers to an aryl group where at least one carbon atom is replaced with a heteroatom (e.g. nitrogen, oxygen, sulfur) and can be indolyl, furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), 1H-indolyl, isoquinolyl (or its N-oxide), or quinolyl (or its N-oxide), for example.

As used herein, the term "substituted" refers to at least one hydrogen atom that is replaced with a non-hydrogen group, provided that normal valencies are maintained and that the substitution results in a stable compound. When a compound or a R group (denoted as $R_1$, $R_2$, and so forth) is noted as "optionally substituted", the substituents are selected from the exemplary group including, but not limited to, aroyl (as defined hereinafter), halogen (e.g. chlorine, bromine, fluorine or iodine), alkyl, alkoxy (i.e. straight or branched chain alkoxy having 1 to 10 carbon atoms, and includes, for example, methoxy, ethoxy, propoxy, isopropoxy, butoxy, isobutoxy, secondary butoxy, tertiary butoxy, pentoxy, isopentoxy, hexyloxy, heptyloxy, octyloxy, nonyloxy, and decyloxy), cycloalkyloxy including cyclopentyloxy, cyclohexyloxy, and cycloheptyloxy, aryloxy including phenoxy and phenoxy substituted with halo, alkyl, alkoxy, and haloalkyl which refers to straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-tri-fluoroethyl, 2,3,3-trifluoropropyl, 1,1,2,2-tetrafluoroethyl, 2,2,3,3-tetrafluoropropyl, hydrocarbyl, substituted hydrocarbyl, arylalkyl, hydroxy, alkoxy, oxo, alkanoyl, alkanoyloxy, amino, alkylamino, arylamino, arylalkylamino, disubstituted amines (e.g. in which the two amino substituents are selected from the exemplary group including, but not limited to, alkyl, aryl, or arylalkyl), alkanylamino, arylamino, alkanoylamino, substituted alkanoylamino, substituted arylamino, substituted arylamino, thiol, alkylthio, arylthio, arylalkylthio, alkylthiono, arylthiono, aryalkylthiono, alkylsulfonyl, arylsulfonyl, arylalkylsulfonyl, sulfonamido (e.g. —$SO_2NH_2$), substituted sulfonamido, nitro, cyano, carboxy, carbamyl (e.g. —$CONH_2$), substituted carbamyl (e.g. —CONHalkyl, —CONHaryl, —CONHarylalkyl or cases where there are two substituents on one nitrogen from alkyl, aryl, or arylalkyl), alkoxycarbonyl, aryl, substituted aryl, guanidine, heteroarylcarbonyl, substituted heteroarylcarbonyl, heterocyclyl, substituted heterocyclyl and mixtures thereof and the like. The substituents may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety).

The term "heterocyclyl" as used in this disclosure refers to a 3-8, preferably 4-8, more preferably 4-7 membered monocyclic ring or a fused 8-12 membered bicyclic ring which may be saturated or partially unsaturated, which monocyclic or bicyclic ring contains 1 to 4 heteroatoms selected from oxygen, nitrogen, silicon or sulfur. Examples of such monocyclic rings include oxaziridinyl, homopiperazinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl and azepanyl. Examples of such bicyclic rings include indolinyl, isoindolinyl, benzopyranyl, quinuclidinyl, 2,3,4,5-tetrahydro-1,3,benzazepine, 4-(benzo-1,3-dioxol-5-methyl)piperazine, and tetrahydroisoquinolinyl. Further, "substituted heterocyclyl" may refer to a heterocyclyl ring which has one or more oxygen atoms bonded to the ring (i.e. as ring atoms). Preferably, said atom which is bonded to the ring selected from nitrogen or sulfur. An example of a heterocyclyl substituted with one or more oxygen atoms is 1,1-dioxido-1,3-thiazolidinyl.

The term "alkylthio" as used in this disclosure refers to a divalent sulfur with alkyl occupying one of the valencies and includes the groups methylthio, ethylthio, propylthio, butylthio, pentylthio, hexylthio, and octylthio.

The term "alkanoyl" as used in this disclosure refers to an alkyl group having 2 to 18 carbon atoms that is bound with a double bond to an oxygen atom. Examples of alkanoyl include, acetyl, propionyl, butyryl, isobutyryl, pivaloyl, valeryl, hexanoyl, octanoyl, lauroyl, and stearoyl.

Examples of aroyl are benzoyl and naphthoyl, and "substituted aroyl" may refer to benzoyl or naphthoyl substituted by at least one substituent including those selected from halogen, amino, vitro, hydroxy, alkyl, alkoxy and haloalkyl on the benzene or naphthalene ring.

The term "arylalkyl" as used in this disclosure refers to a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl.

The term "heteroarylcarbonyl" as used in this disclosure refers to a heteroaryl moiety with 5 to 10 membered mono- or fused-heteroaromatic ring having at least one heteroatom selected from nitrogen, oxygen and sulfur as mentioned above, and includes, for example, furoyl, nicotinoyl, isonicotinoyl, pyrazolylcarbonyl, imidazolylcarbonyl, pyrimidinylcarbonyl, and benzimidazolyl-carbonyl. Further, "substituted heteroarylcarbonyl" may refer to the above mentioned heteroarylcarbonyl which is substituted by at least one substituent selected from halogen, amino, vitro, hydroxy, alkoxy and haloalkyl on the heteroaryl nucleus, and includes, for example, 2-oxo-1,3-dioxolan-4-ylmethyl, 2-oxo-1,3-dioxan-5-yl.

Vinyl refers to an unsaturated substituent having at least one unsaturated double bond and having the formula $CH_2=CH-$. Accordingly, said "substituted vinyl" may refer to the above vinyl substituent having at least one of the protons on the terminal carbon atom replaced with alkyl, cycloalkyl, cycloalkylalkyl, aryl, substituted aryl, heteroaryl or substituted heteroaryl.

The term "hydrocarbyl" as used herein refers to a univalent hydrocarbon group containing up to about 24 carbon atoms (i.e. a group containing only carbon and hydrogen atoms) and that is devoid of olefinic and acetylenic unsaturation, and includes alkyl, cycloalkyl, alkyl-substituted cycloalkyl, cycloalkyl-substituted cycloalkyl, cycloalkylalkyl, aryl, alkyl-substituted aryl, cycloalkyl-substituted aryl, arylalkyl, alkyl-substituted aralkyl, and cycloalkyl-substituted aralkyl. Further, functionally-substituted hydrocarbyl groups may refer to a hydrocarbyl group that is substituted by one or more functional groups selected from halogen atoms, amino, nitro, hydroxy, hydrocarbyloxy (including alkoxy, cycloalkyloxy, and aryloxy), hydrocarbylthio (including alkylthio, cycloalkylthio, and arylthio), heteroaryl, substituted heteroaryl, alkanoyl, aroyl, substituted aroyl, heteroarylcarbonyl, and substituted heteroarylcarbonyl.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}C$ and $^{14}C$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

The composition may be used to treat cancer, such as colon cancer, breast cancer, and/or liver cancer, a bacterial infection, and/or fungal infection.

In one embodiment, the composition is used for treating cancer and further comprises a second active ingredient, such as an antineoplastic agent or a chemotherapeutic agent, for the treatment or prevention of neoplasm, of tumor or cancer cell division, growth, proliferation and/or metastasis in the subject; induction of death or apoptosis of tumor and/or cancer cells; and/or any other form of proliferative disorder.

Exemplary chemotherapeutic agents include, without limitation, aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, 6-thioguanine, topotecan, vinblastine, vincristine, retinoic acid, oxaliplatin, cisplatin, carboplatin, 5-FU (5-fluorouracil), teniposide, amasacrine, docetaxel, paclitaxel, vinorelbine, bortezomib, clofarabine, capecitabine, actinomycin D, epirubicine, vindesine, methotrexate, tioguanine (6-thioguanine), tipifamib. Exemplary antineoplastic agents which are protein kinase inhibitors include, without limitation, imatinib, erlotinib, sorafenib, sunitinib, dasatinib, nilotinib, lapatinib, gefitinib, temsirolimus, everolimus, rapamycine, bosutinib, pzopanib, axitinib, neratinib, vatalanib, pazopanib, midostaurin and enzastaurin. Exemplary antineoplastic agents which are antibodies include, without limitation, trastuzumab, cetuximab, panitumumab, rituximab, bevacizumab, mapatumumab, conatumumab, lexatumumab, and the like.

The neoplastic activity of the tumor or cancer cells may be localized or initiated in one or more of the following: blood, brain, bladder, lung, cervix, ovary, colon, rectum, pancreas, skin, prostate gland, stomach, intestine, breast, liver, spleen, kidney, head, neck, testicle, bone (including bone marrow), thyroid gland, and central nervous system.

In treating certain cancers, the best approach is a combination of surgery, radiotherapy, and/or chemotherapy. Therefore, in at least one embodiment, the composition is employed with radiotherapy. In another embodiment, the composition is employed with surgery.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, 10%, 15%, 20%, 25%, 30%, 40%, 50%, 60%, 70%, 75%, 80%, 85%, 90%, 95%, 99%, or 100%, relative to the tumor size before treatment. In other embodiments, the size of a tumor after treatment does not reduce but is maintained the same as the tumor size before treatment. Methods of assessing tumor size include but are not limited to CT scan, MRI, DCE-MRI and PET scan.

In one embodiment, the $LC_{50}$ is in a range of 1-200 μg/ml, preferably 5-100 μg/ml, more preferably 10-80 μg/ml of the composition and/or the $LC_{90}$ in a range of 10-500 μg/ml, preferably 20-300 μg/ml, more preferably 30-150 μg/ml toward human cancer cell lines (e.g. HCT116, MCF7, and/or HePG2).

As used herein, the terms "$LC_{50}$" and "$LC_{90}$" refer to lethal concentrations of the compound of formula (I), the salt thereof, the solvate thereof, or the combination thereof which cause the death of 50% and 90%, respectively, of cells in 48 hrs.

The viability of cells can be determined by standard cell viability assays, such as, without limitation, ATP test, Calcein AM assay, clonogenic assay, ethidium homodimer assay, Evans blue assay, Fluorescein diacetate hydrolysis/propidium iodide staining assay, flow cytometry assay, formazan-based assays (MTT, XTT), green fluorescent protein assay, lactate dehydrogenase assay, methyl violet assay, propidium iodide assay, Resazurin assay, Trypan Blue assay and TUNEL assay. In a preferred embodiment, a XTT assay is used.

In at least one embodiment, the human cancer cells are derived from commercial cell lines, including but are not limited to HeLa cervical cancer cells, A549 lung cancer cells, HCT15 colon cancer cells, HCT8 or HRT8 colon cancer cells, HCT116 colon cancer cells, DLD1 colon cancer cells, MCF7 breast cancer cells, A2780 ovarian cancer cells, HePG2 liver cancer cells, and DU145 prostatic cancer cells. In some embodiments, cisplatin-resistant cancer cells are used. These cells may be cultured with low doses of cisplatin in order to build resistance to cisplatin while maintaining cell viability. Examples of cisplatin-resistant cancer cells include, but are not limited to, A2780-cis cisplatin-resistant ovarian cancer cells and SGC7901-cis cisplatin-resistant gastrointestinal cancer cells. In other embodiments, the human cancer cells are cancer cells of a human patient who has been diagnosed with, is suspected of having, or is susceptible to or at risk of having at least one form of cancer, preferably liver cancer and/or colon cancer.

In one embodiment, the composition is used for treating a bacterial infection and further comprises a second antibacterial compound. The second antibacterial compound may be present at a molar ratio to the compound of formula (I) (second antibacterial compound:compound of formula (I)) in a range of 1:100 to 100:1, preferably 1:50 to 50:1, preferably 1:10 to 10:1, and more preferably 1:1.2 to 1.2:1. Exemplary second antibacterial compounds include, without limitation, ampicillin, flucloxacillin, amoxicillin, gentamicin, amikacin, kanamycin, neomycin, netilmicin, tobramycin, paromomycin, streptomycin, spectinomycin, tetracycline, penicillin, erythromycin, and doxycycline. As used herein, the term "antibacterial compound" refers to a compound that inhibits or prevents the growth of bacterial cells.

In one embodiment, a source of the bacterial infection is at least one of *Mycobacterium tuberculosis, Clostridium difficile, Listeria monocytogenes, Neisseria meningitides, Vibrio cholera, Enterococcus faecalis, Clostridium botulinum, Clostridium tetani, Bacillus cereus, Salmonella enterica, Bacillus anthracis, Bacillus subtilis, Staphylococcus aureus, Escherichia coli, Proteus* species, or *Pseudomo-* nas aeruginosa. Preferably, source of the bacterial infection is at least one of gram-positive bacteria, such as *Bacillus subtilits, Staphylococcus aureus*, and *Enterococcus faecalis*, and/or at least one gram-negative bacteria such as *Escherichia coli, Pseudomonas aeruginosa*, and *Proteus* species.

In one embodiment, the composition is used for treating a fungal infection and further comprises a second antifungal compound, which may be amphotericin B, itraconazole, posaconazole, voriconazole, fluconazole, flucytosine, terbinafine, posaconazole, isavuconazole, griseofulvin, ketoconazole, miconazole, nystatin, or clotrimazole. The second antifungal compound may be present at a molar ratio to the compound of formula (I) (second antifungal compound: compound of formula (I)) in a range of 1:100 to 100:1, preferably 1:50 to 50:1, preferably 1:10 to 10:1, and more preferably 1:1.2 to 1.2:1.

In one embodiment, a source of the fungal infection is yeast and/or at least one fungus such as *Candida albicans, Cryptococcus neoformans, Cryptococcus gattii, Aspergillus fumigatus, Aspergillus flavus, Histoplasma capsulatum, Coccidioides immitis, Coccidioides posadasii, Blastomyces dermatitidis, Sporothrix schenckii, Pneumocystis jirovecii, Histoplasma capsulatum, Magnaporthe oryzae, Botrytis cinerea*, species within the *Puccinia* genus, *Fusarium graminearum, Fusarium oxysporum, Fusarium equiseti, Blumeria graminis, Mycosphaerella graminicola*, species within the *Colletotrichum* genus, *Ustilago maydis, Melampsora lini, Phakopsora pachyrhizi, Rhizoctonia solani, Cochilobolus lunatus, Rhizopus oryzae*, or *Phoma sorghina*. Preferably, the fungus is a filamentous fungus such as *Aspergillus niger* and *Aspergillus flavus*.

In one embodiment, the composition is used for treating bacterial and fungal infection and further comprises a second antimicrobial compound, which may be a quaternary ammonium compound (such as benzalkonium chloride), glutaraldehyde, chlorhexidine gluconate, phenol, or octenidine dihydrochloride. As used herein, the term "antimicrobial compound" refers to a compound that inhibits or prevents the proliferation of microorganisms, including but not limited to bacterial cells, fungal cells, viruses, and parasites.

In most embodiments, the minimum inhibitory concentration of the compound of formula (I), the salt thereof, the solvate thereof or the combination thereof may be in a range of 10-700 μg/ml, preferably 50-600 μg/ml, more preferably 50-400 μg/ml of the composition. As used herein, the term "minimum inhibitory concentration" refers to the lowest concentration of the compound of formula (I), the salt thereof, the solvate thereof, or the combination thereof that will inhibit the visible growth of a microorganism (e.g. fungus, bacteria, virus) after overnight incubation.

The minimum inhibitory concentration may be determined by a broth dilution method (e.g. microdilution or macrodilution), an agar dilution method, an agar well diffusion method, or a disk diffusion method. Preferably, the agar well diffusion method is used.

In most embodiments, the method further comprises measuring a concentration of a biomarker and/or detecting a mutation in a biomarker before and/or after the composition is administered. As used herein, the term "biomarker" refers to a characteristic that is objectively measured and evaluated as an indicator of normal biological processes, pathogenic processes or pharmacological responses to a therapeutic intervention. Exemplary cancer biomarkers include, without limitation, AFP, BCR-ABL, BRCA1, BRCA2, BRAF, CA-125, CA19.9, CEA, EGFR, HER-2, KIT, PSA, S100, KRAS, p53, p16, CDKN2B, p14ARF, MYOD1, CDH1, CDH13, RB1, metallopeptidase inhibitor 1, microRNA, estrogen receptor, progesterone receptor, UGT1A1, CD20 antigen, CD30, PDGFR, leucine, isoleucine, valine, and ALK. Specifically, potentially predictive cancer biomarkers include, without limitation, mutations on genes KRAS, p53, EGFR, erbB2 for colorectal, esophageal, liver, and pancreatic cancer; mutations of genes BRCA1 and BRCA2 for breast and ovarian cancer; abnormal methylation of tumor suppressor genes p16, CDKN2B, and p14ARF for brain cancer; hypermethylation of MYOD1, CDH1, and CDH13 for cervical cancer, and hypermethylation of p16, p14ARF, and RB1, for oral cancer. Cancer biomarkers may be useful in determining the aggressiveness of an identified cancer as well as its likelihood of responding to the treatment. Examples of such prognostic biomarkers include, without limitation, elevated levels of metallopeptidase inhibitor 1 (TIMP1), a biomarker associated with more aggressive forms of multiple myeloma; and elevated estrogen receptor (ER) and/or progesterone receptor (PR) expression, biomarkers associated with better overall survival in patients with breast cancer.

Exemplary biomarkers for bacterial infection include, without limitation, C-reactive protein (CRP), soluble triggering receptor expressed on myeloid cells 1 (sTREM-1), pro-adrenomedullin (ProADM), serum procalcitonin (PCT), mid-regional pro-atrial natriuretic peptide (ANP), pancreatic stone protein (PSP)/regenerating protein (reg), interleukin-6 (IL-6), IL-8, IL-27, soluble urokinase-type plasminogen activator receptor (suPAR). In some embodiments, the leucocyte count and/or erythrocyte sedimentation rate (ESR) are indications of a bacterial infection.

Exemplary biomarkers for fungal infection include, without limitation, galactomannan and 1,3-β-D-glucan.

The mutation in the biomarker may be detected with a polymerase chain reaction (PCR) assay, DNA microarray, multiplex ligation-dependent probe amplification (MLPA), single strand conformational polymorphism (SSCP), denaturing gradient gel electrophoresis (DGGE), heteroduplex analysis, and restriction fragment length polymorphism (RFLP). The procedures to detect the mutation are well-known to those of ordinary skill in the art.

The concentration of the biomarker may be measured with an assay, for example an antibody-based method (e.g. an ELISA).

As used herein, the term "antibody-based method" refers to any method with the use of an antibody including, but not limited to, enzyme-linked immunosorbent assay (ELISA), Western blotting, immunoprecipitation (IP), enzyme linked immunospot (ELISPOT), immunostaining, immunohistochemistry, immunocytochemistry, affinity chromatography, and the like.

Preferably, an ELISA is used. The term "ELISA" refers to a method of detecting the presence and concentration of a biomarker in a sample. There are several variants of ELISA, including, but not limited to, sandwich ELISA, competitive ELISA, indirect ELISA, ELISA reverse, and the like. The ELISA assay may be a singleplex assay or a multiplex assay, which refers to a type of assay that simultaneously measures multiple analytes in a single run/cycle of the assay. Preferably, a sandwich ELISA is used.

The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

The term "sample" includes any biological sample taken from the subject including a cell, tissue sample, or body fluid. For example, a sample may include a skin sample, a cheek cell sample, saliva, or blood cells. A sample can include, without limitation, a single cell, multiple cells, fragments of cells, an aliquot of a body fluid, whole blood, platelets, serum, plasma, red blood cells, white blood cells, endothelial cells, tissue biopsies, synovial fluid, and lymphatic fluid. In some embodiments, the sample is taken from a tumor.

In some embodiments, the concentration of the biomarker is measured before and after the administration. When the concentration of the biomarker is maintained, the method may further comprise increasing the effective amount of the compound of formula (I), the salt thereof, the solvate thereof, or the combination thereof by at least 5%, at least 10%, or at least 30%, up to 50%, up to 60%, or up to 80% of an initial effective amount that is in a range of 1-100 mg/kg based on the weight of the subject. The increased effective amount may be in a range of 1.05-180 mg/kg, preferably 15-140 mg/kg, more preferably 25-90 mg/kg. The subject may be administered with the increased dosage for a longer period (e.g. 1 week more, 2 weeks more, or 2 months more) than the duration with the initial effective amount.

In some embodiments, the mutation in the biomarker is detected before administrating the composition to identify subjects predisposed to the disease. For example, women with a BRCA1 germline mutation are at a higher risk of contracting breast and ovarian cancer.

In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

Having generally described this disclosure, a further understanding can be obtained by reference to certain specific examples which are provided herein for purposes of illustration only and are not intended to be limiting unless otherwise specified.

Example 1 Materials and Methods

All melting points were measured on a Gallenkamp Electrothermal melting point apparatus and were uncorrected. The IR absorption spectra were measured on a Nicolet Magna 520 FT IR Spectrophotometer. $^1$H and $^{13}$C NMR spectra were recorded in deuterated dimethylsulfoxide (DMSO-$d_6$) at 400 MHz on a Bruker DPX MHz spectrometer using tetramethylsilane (TMS) as an internal reference. Chemical shift was expressed as δ values. Mass spectra were obtained from on a Shimadzu GCMS-QP 1000 Ex mass spectrometer at 70 eV. Elemental analyses were carried out at the Microanalytical Center at Cairo University.

Example 2 Synthesis of Antimicrobial and Cytotoxic Small Molecules

The synthesis of the chromenone derivatives was reported in Alzaydi et al. (K. M. Alzaydi, R. M. Borik, M. H. Elnagdi, J. Heterocyclic Chemistry, 44, 1187 (2007), incorporated herein by reference in its entirety). In the article, the coupling reaction of compound 3 with aromatic diazonium salts with the aim of obtaining compound 4 was studied (FIG. 1). Interestingly, the target molecule was not obtained, and cyclic N,O-acetal 6 was formed in good yields. The formed enazo compound 4 may have initially cyclized into compound 5 that reacted with ethanol to yield the final isolable compound 6.

$^{13}$C and $^1$H NMR spectra of the products fitted the proposed structures completely. The $^{13}$C NMR spectrum revealed two carbon signals at δ=15.4 and 64.4 ppm for the ether moiety. The sp$^3$ carbon-2 appeared at δ=98.2 ppm. The $^1$H NMR spectrum showed the ether triplet and quartet at δ=1.0 and 3.8 ppm and a singlet at δ=5.9 ppm for 2-H in the chromenone ring. The $D_2O$-exchangable signal at δ=14.1 ppm was attributed to a NH proton which was hydrogen-bonded to a carbonyl group. Compound 7 may existed in the enol azo form.

General Procedure for the Preparation of Compounds 6a-c

A cold solution of arenediazonium salt (0.1 mol) was prepared by adding a solution of sodium nitrite (1.5 g in 10 ml $H_2O$) to a cold solution of aryl amine (0.1 mol) in concentrated HCl (5 ml) with stirring. The resulting solution of the arenediazonium salt was then added to a cold solution of enaminones 3 in EtOH (50 mL) containing sodium acetate (0.1 mol). The mixture was stirred at r.t. for 1 h and the solid product so formed was collected by filtration and crystallized from ethanol.

Ethoxy-3-[(4-nitro-phenyl)-hydrazono]-chroman-one (6a)

M.p. 90° C.; orange crystals from ethanol; yield 92%. IR: ν=3200 (NH), 3100 (CH aromatic), 2950 (CH aliphatic), 1665 (C=O) and 1607 (C=N) cm$^{-1}$. $^1$H-NMR (400 MHz, DMSO-$d_6$): δ=1.12 (t, 3H, $CH_3CH_2$), 5.99 (s, 1H, CH), 4.34 (q, 2H, $CH_2CH_3$), 7.21-8.27 (m, 8H, Ar—H) and 13.59 (brs, 1H, NH). $^{13}$C-NMR (100 MHz, DMSO-$d_6$): δ=15.43 ($CH_3CH_2O$), 64.40 ($CH_3CH_2O$), 100.81 (CH), 119.39, 122.33, 123.50, 126.14, 127.37, 131.79, 137.81, 143.15, 148.29 (aromatic carbons), 156.78 (C=N—N) and 178.0031 (C=O). MS (EI, 70 eV): m/z (%)=341 (32.2) [M$^+$]. $C_{17}H_{15}N_3O_5$ (341.32): calcd. C, 59.82; H, 4.43; N, 12.31. found: C, 60.01; H, 4.58; N, 12.11.

2-ethoxy-3-(2-(2-methoxyphenyl)hydrazono)chroman-4-one (6b)

M.p. 158° C.; dark orange crystals from ethanol; yield 90%. IR: ν=3200 (NH), 3081 (CH aromatic), 2944 (CH aliphatic), 1651 (C=O) and 1605 (C=N) cm$^{-1}$. $^1$H-NMR (400 MHz, DMSO-$d_6$): δ=1.10 (t, 3H, $CH_3CH_2$), 3.88 (q, 2H, $CH_2CH_3$), 3.83 (s, 3H, $OCH_3$), 5.8 (s, 1H, CH), 7.20-8.75 (m, 8H, Ar—H) and 10.68 (s, 1H, NH). $^{13}$C-NMR (100 MHz, DMSO-$d_6$): δ=15.20 ($CH_3CH_2O$), 56.8 ($OCH_3$), 64.41 ($CH_3CH_2O$), 98.23 (CH), 100.42, 119.37, 122.22, 123.54, 124.47, 127.52, 131.68, 133.68, 135.43, 138.919, 145.05 (aromatic carbons), 156.77 (C=N—N), and 178.62 (C=O). MS (EI, 70 eV): m/z (%)=326 (100) [M$^+$]. $C_{18}H_{18}N_2O_4$ (326.35): calcd. C, 66.25; H, 5.56; N, 8.58. found: C, 66.12; H, 5.81; N, 8.15.

3-[(4-Chlorophenyl)hydrazono]-2-ethoxychroman-4-one (6c)

M.p. 120° C.; orange crystals from ethanol; yield 90%. IR: ν=3220 (NH), 3080 (CH aromatic), 2946 (CH aliphatic), 1660 (C=O) and 1607 (C=N) cm$^{-1}$. $^1$H-NMR (400 MHz, DMSO-d$_6$): δ=1.07 (t, 3H, CH$_3$CH$_2$), 5.95 (s, 1H, CH), 4.03 (q, 2, CH$_2$CH$_3$), 7.18-7.52 (m, 8H, Ar—H) and 13.75 (s, 1H, NH). $^{13}$C-NMR (100 MHz, DMSO-d$_6$): δ=15.44 (CH$_3$CH$_2$O), 64.19 (CH$_3$CH$_2$O), 100.88 (CH), 117.44, 119.21, 122.46, 123.30, 127.14, 128.38, 129.1639, 129.88, 137.18, 141.69 (aromatic carbons), 156.48 (C=N—N), and 177.46 (C=O). MS (EI, 70 eV): m/z (%)=330 (38.2) [M$^+$]. C$_{17}$H$_{15}$ClN$_2$O$_3$ (330.77): calcd. C, 61.73; H, 4.57; N, 8.47. found: C, 61.42; H, 4.81; N, 8.55.

Example 3 Experimental Procedure and Data for Cytotoxicity Studies in Human Cancer Cell Lines Reagents: Fetal bovine serum (FBS) and L-glutamine were purchased from Gibco Invitrogen Co. (Scotland, UK). RPMI-1640 medium was from Cambrex (New Jersey, USA). Dimethyl sulfoxide (DMSO), doxorubicin, penicillin, streptomycin and sulforhodamine B (SRB) were from Sigma Chemical Co. (Saint Louis, USA).

Cell cultures: Three human tumor cell lines, HCT116 (colon cell line), HePG 2 (human hepatocellular carcinoma cell line), and MCF7 (human Caucasian breast adenocarcinoma) were used. In vitro bioassay on human tumor cell lines were conducted and determined by the Bioassay-Cell Culture Laboratory, National Research Centre, El-Tahrir St., Dokki, Cairo 12622, Egypt. They grew as a monolayer and are routinely maintained in RPMI-1640 medium supplemented with 5% heat-inactivated FBS, 2 mM glutamine and antibiotics (penicillin 100 U/mL, streptomycin 100 µg/mL), at 37° C. in a humidified atmosphere containing 5% CO$_2$. Exponentially growing cells were obtained by plating 1.5×10$^5$ cells/mL for MCF-7 and HCT116 and 0.75×10$^4$ cells/mL for HePG2, followed by 24 h of incubation. The effect of the vehicle solvent (DMSO) on the growth of these cell lines was evaluated in all experiments by exposing untreated control cells to the maximum concentration (0.5%) of DMSO used in each assay.

Tumor cell growth assay: The effect on the in vitro growth of human tumor cell lines was evaluated according to the procedure adopted by the National Cancer Institute (NCI, USA) in the 'In vitro Anticancer Drug Discovery Screen' that uses the protein-binding dye sulforhodamine B to assess cell growth. Briefly, cells growing in 96-well plates were then exposed for 48 h to five serial concentrations of each compound, starting from a maximum concentration of 78 µM (P. Skehan, R. Storeng, D. Scudiero, A. Monks, J. McMahon, D. Vistica, J. T. Warren, H. Bokesch, S. Kenney, M. R. Boyd, J. Natl. Cancer Inst., 82, 1107 (1990), incorporated herein by reference in its entirety). Following this exposure period adherent cells were fixed, washed, and stained. The bound stain was solubilized and the absorbance was measured at 492 nm in a plate reader (Bio-Tek Instruments Inc., Power wave XS, Wincoski, USA). For each test compound and cell line, a dose-response curve was obtained and the growth inhibition of 50% (GI50), corresponding to the concentration of the compounds that inhibited 50% of the net cell growth, was calculated as described elsewhere (A. Monks, D. Scudiero, P. Skehan, R. Shoemaker, K. Paull, D. Vistica, C. Hose, J. Langley, P. Cronise, A. Vaigro-Wolff, M. Gray-Goodrich, H. Campbell, J. Mayo, M. J. Boyd, Natl. Cancer Inst., 83, 757 (1991), incorporated herein by reference in its entirety). Doxorubicin was used as a positive control and tested in the same manner.

The effect of compounds was evaluated on the in vitro growth of three human tumor cell lines representing different tumor types, namely, HCT116, HePG 2, and MCF7 after an exposure for 48 h. All tested compounds inhibited the growth of the tested human tumor cell lines in a dose-dependent manner (data not shown). The results presented in Tables 1, 2, and 3 revealed that the chromenone derivatives 6c and 6a showed the highest inhibitory effect relative to the reference standard material (Doxorubicin) against all three tumor cell lines.

TABLE 1

HCT116 (colon cancer cell line)

| Sample Code | LC$_{50}$ (µg/ml) | LC$_{90}$ (µg/ml) | Remarks |
|---|---|---|---|
| 6a | 70.7 | 123.3 | 65.3% at 100 ppm |
| 6b | — | — | 39.6% at 100 ppm |
| 6c | 13.2 | 23.1 | 100% at 100 ppm |
| DMSO | — | — | 1% at 100 ppm |
| Negative Control | — | — | 0% |

LC$_{50}$: Lethal concentration of the sample which causes the death of 50% of cells in 48 hrs
LC$_{90}$: Lethal concentraton of the sample which causes the death of 90% of cells in 48 hrs

TABLE 2

HePG 2 (human hepatocellular cancer cell line)

| Sample Code | LC$_{50}$ (µg/ml) | LC$_{90}$ (µg/ml) | Remarks |
|---|---|---|---|
| 6a | — | — | 45.3% at 100 ppm |
| 6b | — | — | 56.1% at 100 ppm |
| 6c | 39.0 | 68.9 | 94.2% at 100 ppm |
| DMSO | — | — | 1% at 100 ppm |
| Negative control | — | — | 0% |

TABLE 3

MCF7 (human Caucasian breast cancer cell line)

| Sample Code | LC$_{50}$ (µg/ml) | LC$_{90}$ (µg/ml) | Remarks |
|---|---|---|---|
| 6a | 76.3 | 124.1 | 61.3% at 100 ppm |
| 6b | — | — | 22.9% at 100 ppm |
| 6c | 15.8 | 27.0 | 100% at 100 ppm |
| DMSO | — | — | 3% at 100 ppm |
| Negative control | — | — | 0% |

Example 4 Experimental Procedure and Data for Antimicrobial Studies

The ability to inhibit the growth of Gram-positive and Gram-negative bacteria, yeasts and filamentous fungi was observed using an overlay method (S. R. Connell, D. M. Tracz, K. H. Nierhaus, D. E. Taylor, Antimicrob. Agents Chemother. 47, 3675 (2003), incorporated herein by reference in its entirety).

The common pathogenic and food spoilage microorganisms were selected for their relevance in bakery products and other food: the gram-positive bacteria: *Bacillus subtilits* NRRL-B-4219, *Staphylococcus aureus* ATCC 6538, *Enterococcus faecalis* ATCC 19433; the gram negative bacteria: *Escherichia coli* ATCC 25922, *Pseudomonas aeruginosa* ATCC 9027, *Proteus* sp.; yeasts, such as *Candida albicans* ATCC 10231; and fungi: *Aspergillus niger* NRRL 2766 (equivalent to ATCC 16888), and *Aspergillus flavus* ATCC 16883. The bacteria were slanted on nutrient agar (Merck, Darmstadt, Germany), yeast was slanted and mentioned on Sabaroud's agar medium (Lab M., Bury, Lancashire, UK) and the fungi was slanted and mentioned on the potato Dextrose Agar medium (Lab M Limited, Bury, Lancashire, UK). Mueller-Hinton agar (Lab M., Bury, Lancashire, UK) following the manufacturer's instructions was used for the assay.

All compounds were dissolved in dimethyl sulfoxide (RFCL Limited, New Delhi, India) at 50 µg/mL concentration as shown in Table 4 in comparison with different standard antibiotics. Antibiotic discs of Streptomycin (S) (10 µg), Oxytetracycline (T) (30 µg), and Tetracyciline (TE) (30 µg) were used as positive controls for bacteria. Neomycin (N) (30 µg), was used for fungi.

The antibacterial screening was performed with the well diffusion agar method (S. T. Williams, M. Goodfellow, E. M. H. Wellington, J. C. Vickers, G. Alderson, P. H. A. Sneath, S. M. J. Sackins, A. M. Mortimer, J. Gen. Microbiol. 129, 1815(1983); and B. Bonev, J. Hooper, J. Parisot, J. Antimicrob. Chemother., 61, 1295(2008), each incorporated herein by reference in their entirety). The organisms were streaked in radial patterns on the agar plates. Plates were incubated under aerobic conditions at 37° C. and 28° C. for 24 h and 48 h for bacteria and fungi, respectively. All prepared solutions were treated under the same conditions under the same incubated plates. All tests were performed in triplicate. Plates were examined for evidence of antimicrobial activities, represented by a zone of inhibition of the microorganism's growth around the holes, and diameters of clear zones were expressed in millimeters (R. Cruickshank, J. P. Duguid, B. P. Marmion, R. H. A. Swain, The practice of medicinal microbiology. In Medical Microbiology, 12th ed.; Churchill Livingstone: Edinburgh, UK, Volume 11, pp. 196-202 (1975), incorporated herein by reference in its entirety).

The synthesized compounds were screened for in vitro antimicrobial against gram-positive (*Bacillus subtilits*) and gram-negative (*Escherichia coli*) bacteria, yeast (*Candida albicans*) and filamentous fungi (*Aspergillus niger*). The tested products showed a strong to moderate effect against most of the tested pathogens. The compounds showed a strong inhibitory effect against Gram-positive bacteria (*Bacillus subtilits* and *Staphylococcus aureus*) and Gram-negative bacteria (*Pseudomonas aeruginosa* and *Escherichia coli*). The conventional compounds used for positive controls showed a weak to a moderate inhibition effect against *Proteus* sp and *Entercoccus faecalis*. The antifungal activities are presented in Table 4. For unicellular fungi, most of the compounds showed a strong antifungal effect against *Candida albicans* except compound 6b.

For filamentous fungi, compounds 6a and 6c showed a more potent antifungal effect against *Aspergillus niger* and a moderate activity against *A. flavus* in comparison with the antifungal standard antibiotic (Neomycin) used in this study. Finally, the demonstration of the activity of compound 6c against gram-positive bacteria, gram-negative bacteria, and fungi is an indication that this compound can be used in the treatment of the tested pathogens due to its broad spectrum effect.

Without wishing to be bound by theory, the structure-activity of these synthesized compounds chromenone derivatives may be due to their ability for inhibiting the cell growth by inhibiting the protein synthesis (M. M. Hinman, T. A. Osenberg, D. Balli, C. Black-Schaefer, L. E. Chovan, D. Kalvin, P. J. Merta, A. M. Nilius, S. D. Pratt, N. B. Soni, J. Med. Chem., 49, 4842 (2006), incorporated herein by reference in its entirety).

TABLE 4

Antimicrobial activity of the compounds at 50 µg/mL

| | Inhibition zone (mm) | | | | | | | | |
|---|---|---|---|---|---|---|---|---|---|
| | Bacteria | | | | | | Fungi | | |
| | G+ve | | | G-ve | | | Unicellular | Filamentous | |
| Comp. No. | B. subtilits | S. aureus | Ent. faecalis | E. coli | P. aeruginosa | Proteus sp. | C. albicans | A. niger | A. flavus |
| 6a | 32 | 28 | 25 | 33 | 30 | 27 | 24 | 22 | 22 |
| 6b | 16 | 13 | 0 | 12 | 0 | 0 | 0 | 0 | 0 |
| 6c | 32 | 30 | 21 | 30 | 28 | 26 | 20 | 18 | 17 |
| S* = 10 µg | 14 | 0 | 0 | 0 | 0 | 0 | 12 | 0 | 0 |
| TE* = 30 µg | 10 | 0 | 0 | 0 | 0 | 0 | 0 | 16 | 14 |
| N* = 30 µg | 0 | 0 | 0 | 0 | 0 | 0 | 0 | 16 | 14 |
| T* = 30 µg | 30 | 0 | 0 | 0 | 0 | 0 | 0 | 0 | 0 |

The in vitro minimum inhibitory concentration (MIC) of the synthesized compounds was determined by the agar well diffusion method. DMSO was used to prepare different concentrations ranging from 50 to 500 µg/mL by serial dilutions. The media were inoculated with 100 µL of each of the 106 cfu/mL bacterial and fungal strains, and the assay was applied by an agar well diffusion method. Blank DMSO was used as negative control. The plates were incubated aerobically in an incubator at 37° C. for 24 h for bacterial strains and 25° C. for 48 h for fungal strains. The MIC was taken as the lowest concentration in the series dilution that prevented bacterial growth.

The minimum inhibitory concentration (MIC) of the synthesized compounds is presented in the Table 5. The MIC varied from 50 to 500 µg/mL based on the tested compounds. The MIC of the compound 6c was 50, 50, 75 and 100 µg/mL against tested pathogens *E. coli, C. albicans, B. subtilis* and *A. niger* respectively. On the other hand, the MIC of the compound 6a was 100 and 150 µg/mL against *E. coli* and *Bacillius subtilis*. Compounds 6a and 6c have strongest antifungal and antibacterial activities. The demonstration of the activity against gram-positive bacteria, gram-negative bacteria, and fungi is an indication that the compounds have a broad spectrum effect.

TABLE 5

| | Minimum inhibitory concentration (MIC) of the compounds against pathogens | | | | | | | | |
|---|---|---|---|---|---|---|---|---|---|
| | MIC (µg/mL) | | | | | | | | |
| | Bacteria | | | | | | Fungi | | |
| | G+ve | | | G−ve | | | Unicellular | Filamentous | |
| Comp. No. | B. subtilits | S. aureus | Ent. faecalis | E. coli | P. aeruginosa | Proteus sp. | C. albicans | A. niger | A. flavus |
| 6a | 150 | 350 | 250 | 100 | 300 | 250 | 250 | 200 | 250 |
| 6b | 200 | 300 | 450 | 250 | 400 | 350 | 400 | 300 | 350 |
| 6c | 75 | 150 | 200 | 50 | 150 | 150 | 50 | 100 | 200 |

The foregoing discussion discloses and describes merely exemplary embodiments of the present disclosure. As will be understood by those skilled in the art, the present disclosure may be embodied in other specific forms without departing from the spirit or essential characteristics thereof. Accordingly, the disclosure of the present disclosure is intended to be illustrative, but not limiting of the scope of the disclosure, as well as other claims. The disclosure, including any readily discernible variants of the teachings herein, defines, in part, the scope of the foregoing claim terminology such that no inventive subject matter is dedicated to the public.

The invention claimed is:

1. A method for reducing or inhibiting a progression and/or duration of, reducing or ameliorating a severity of, and/or ameliorating one or more symptoms of at least one cancer selected from the group consisting of colon cancer, breast cancer, and liver cancer in a subject in need thereof, the method comprising:
administering an effective amount of a compound of formula (I):

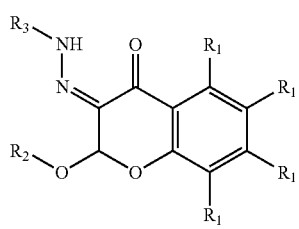

(I)

a salt thereof, a solvate thereof, or a combination thereof, to the subject;
wherein each of $R_1$ is independently selected from the group consisting of H, hydroxy, amino, thiol, fluoro, chloro, bromo, iodo, cyano, carboxy, an optionally substituted carbamyl, an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted heteroarylcarbonyl, an optionally substituted arylolefin, an optionally substituted arylalkylcarboxylic acid, and an optionally substituted vinyl;

$R_2$ selected from the group consisting of an optionally substituted alkyl, an optionally substituted cycloalkyl, an optionally substituted cycloalkylalkyl, an optionally substituted arylalkyl, an optionally substituted heteroaryl, an optionally substituted aryl, an optionally substituted heterocyclyl, an optionally substituted alkylthio, an optionally substituted alkanoyl, an optionally substituted aroyl, an optionally substituted heteroarylcarbonyl, an optionally substituted arylolefin, and an optionally substituted vinyl; and $R_3$ is an optionally substituted aryl.

2. The method of claim 1, wherein $R_2$ is an optionally substituted alkyl.

3. The method of claim 1, wherein $R_3$ is a substituted phenyl comprising an electron withdrawing functional group.

4. The method of claim 3, wherein the electron withdrawing functional group is at least one selected from the group consisting of fluoro, chloro, bromo, iodo, nitro, cyano, ammonium, an optionally substituted alkylammonium, an optionally substituted arylammonium, an optionally substituted alkylarylammonium, trihalomethyl, formyl, an optionally substituted alkanoyl, an optionally substituted aroyl, and sulfonate.

5. The method of claim 3, wherein $R_1$ is H, $R_2$ is ethyl, and $R_3$ is selected from the group consisting of p-$C_6H_4$$NO_2$, o-$C_6H_4OCH_3$, and p-$C_6H_4Cl$.

6. The method of claim 1, further comprising measuring a concentration of a biomarker and/or detecting a mutation in the biomarker before and/or after the compound of formula (I), the salt thereof, the solvate thereof, or the combination thereof is administered.

7. The method of claim 6, wherein the biomarker is at least one selected from the group consisting of AFP, BCR-ABL, BRCA1, BRCA2, BRAF, CA-125, CA19.9, CEA, EGFR, HER-2, KIT, PSA, S100, KRAS, p53, p16, CDKN2B, p14ARF, MYOD1, CDH1, CDH13, RB1, metallopeptidase inhibitor 1, microRNA, estrogen receptor, progesterone receptor, UGT1A1, CD20 antigen, CD30, PDGFR, leucine, isoleucine, valine, and ALK.

8. The method of claim 7, wherein the concentration of the biomarker is measured with an ELISA assay and/or the mutation in the biomarker is measured with a PCR assay.

9. The method of claim 1, wherein the subject is a mammal.

10. The method of claim 1, wherein the effective amount of the compound of formula (I), the salt thereof, the solvate thereof, or the combination thereof is in a range of 1-100 mg/kg.

* * * * *